United States Patent
Boyd et al.

(10) Patent No.: US 11,872,744 B2
(45) Date of Patent: Jan. 16, 2024

(54) PARISON FORMER

(71) Applicant: Blockwise Engineering LLC, Tempe, AZ (US)

(72) Inventors: Jordan Bradley Boyd, Phoenix, AZ (US); Ed Goff, Phoenix, AZ (US); Jeremiah J. Warriner, Tempe, AZ (US)

(73) Assignee: BLOCKWISE ENGINEERING LLC, Tempe, AZ (US)

( * ) Notice: Subject to any disclaimer, the term of this patent is extended or adjusted under 35 U.S.C. 154(b) by 0 days.

(21) Appl. No.: 18/106,223

(22) Filed: Feb. 6, 2023

(65) Prior Publication Data
US 2023/0182371 A1  Jun. 15, 2023

Related U.S. Application Data (63) Continuation-in-part of application No. PCT/US2022/037138, filed on Jul. 14, 2022.
(60) Provisional application No. 63/230,698, filed on Aug. 7, 2021.

(51) Int. Cl.
*B29C 55/24* (2006.01)
*B29C 55/26* (2006.01)
*B29L 31/00* (2006.01)

(52) U.S. Cl.
CPC .............. *B29C 55/26* (2013.01); *B29C 55/24* (2013.01); *B29L 2031/753* (2013.01)

(58) Field of Classification Search
CPC ......... B21D 39/04; B21D 39/048; A61F 2/95; A61F 2/958; B29C 55/22
See application file for complete search history.

(56) References Cited

U.S. PATENT DOCUMENTS

| | | | |
|---|---|---|---|
| 4,207,134 A * | 6/1980 | Valyi | B29C 49/24 425/530 |
| 5,057,267 A | 10/1991 | Seizert et al. | |
| 5,351,462 A | 10/1994 | Anderson et al. | |
| 6,946,092 B1 * | 9/2005 | Bertolino | A61M 25/1029 264/573 |
| 8,043,553 B1 | 10/2011 | Durcan | |

(Continued)

OTHER PUBLICATIONS

ISA/US, International Search Report and Written Opinion of the International Search Authority, (USPTO), dated Oct. 6, 2022, PCT/US2022/037138.

*Primary Examiner* — Alison L Hindenlang
*Assistant Examiner* — Debjani Roy
(74) *Attorney, Agent, or Firm* — Invention To Patent Services; Alex Hobson (57) ABSTRACT

A parison tube former utilizes a radial compression heater to heat a very specific portion of a preform tube for stretching. The heater has a plurality of compression dies that form a central cavity for receiving the preform tube. The working surfaces of the compression dies close down onto the outer surface of the preform tube to heat the tube via conduction, which more accurately and precisely heats the preform tube. A first stretched portion of the preform tube is produced by stretching the preform tube after heating. A second portion of the preform tube is then located within the central cavity and is also heated by the radial compression heater and stretched to produce a second stretched portion of the preform tube and an unexpanded portion of the preform tube, or balloon portion of the parison tube.

19 Claims, 8 Drawing Sheets

(56) References Cited

U.S. PATENT DOCUMENTS

| | | | |
|---|---|---|---|
| 9,956,604 B1* | 5/2018 | Warriner | B21J 9/06 |
| 2006/0150669 A1 | 7/2006 | Kitamura et al. | |
| 2009/0001633 A1* | 1/2009 | Limon | B29C 49/68 |
| | | | 264/402 |

* cited by examiner

PARISON FORMER

CROSS REFERENCE TO RELATED APPLICATIONS

This application is a continuation in part of International Patent Application No. PCT/US2022/037138, filed on Jul. 14, 2022 which claims the benefit of priority to U.S. provisional patent application No. 63/230,698, filed on Aug. 7, 2021; the entirety of each prior application is hereby incorporated by reference herein.

BACKGROUND OF THE INVENTION

Field of the Invention

The invention relates to a parison former and method of forming a parison using said parison former.

Background

Medical balloons are used in a wide variety of medical procedures including, but not limited to angioplasty, stent placement and expansion, stent graft placement and expansion and the like. Parison tubes are hollow plastic tubes used as raw material to form medical balloons. Parison manufacturing machines are slower than desired and often produce balloon portions with tapered ends that are longer than desired. A shorter tapered end may be desired as it provides better accuracy and clarity of an expanded zone when forming the medical balloon.

SUMMARY OF THE INVENTION

The invention is directed to a parison tube former and a method of forming a parison tube using said parison tube former. An exemplary parison tube former utilizes a radial compression heater to heat a very specific portion of the length of a preform tube for stretching. A radial compression heater has a plurality of compression dies that form a central cavity for receiving a preform tube. The working surfaces of the compression dies close down onto the outer surface of the preform tube to heat the preform tube via conduction. This heating method more accurately and precisely heats the preform tube such that diameter reduction of the preform tube during the stretching operation is very controlled. A first stretched portion of the preform tube is produced by stretching the preform tube after heating with the radial compression heater. A second portion of the preform tube is then located within the central cavity and is also heated by the radial compression heater. After the second portion is heated, the preform tube is stretched to produce a second stretched portion of the preform tube and an unexpanded portion of the preform tube, or balloon portion of the parison tube. The tapered ends of the balloon portion may be much sharper or shorted that those of parison tubes made through hot air heating, as the heated zone is not as well controlled as it is through conduction heating. Furthermore, the compression dies may be configured to remain in contact with the preform tube during the stretching operations, wherein the compression dies are forced inward by the die actuator, and may contact the preform tube as the preform tube reduces in diameter down. Maintaining conducting heating during this stretching operation enables very controlled stretching with less stress concentration in the polymer as a result. The parison tube has a balloon portion that has a larger diameter than the diameter of the first and second stretched portions such as 50% larger or more, 100% larger or more, 150% larger or more, 200% larger or more and any range between and including the values provided.

A parison tube former may include a necking apparatus configured on first and/or second end of the radial compression heater that is configured with a necking die configured to press against the balloon portion to produce a necked balloon end that has a necked end length reduced from a tapering balloon length. A balloon portion formed by heating and stretching to reduce the diameter of the parison to form a first stretched and a second stretched portion will have some tapering from the balloon portion to the stretched portions. The length of this tapering portion can be reduced by the necking apparatus. A necking die of a necking apparatus has a necking die aperture that is smaller in diameter than the preform tube such that it can neck the tapering end of the stretched portion against the balloon portion and reduce the tapered end length of the stretched portion to a necked end length that is a fraction of the tapered end length such as about half or less, about a quarter or less, about one sixth or less and any range between and including the values provided. The necking die aperture may have a diameter that is less than the diameter of a stretched portion and may further reduce the diameter of the stretched portion to a necked tube diameter that may be some percentage of the diameter of the stretched portion, such as 90% or less, about 80% or less, about 70% or less, about 60% or less, about 50% or less, about 40% or less, about 30% or less and any range between and including the values provided. Put another way, the diameter of the stretched portion may be reduced by the necking apparatus by at least 5% or more, about 10% or more, about 20% or more, at least 25% or more, at least 40% or more, at least 50% or more to produce the necked tube diameter. The diameter of the stretched portion near the tapered end is reduced the most by the necking apparatus. The tapered end is both reduced in diameter and in length. It may be desirable for the diameter of the necked tube diameter to be as small as possible to enable a more compact package for introduction into the vascular system or other body conduit. The length of a necked balloon end formed by the necking apparatus may be very small, such as no more than about 5 mm, no more than about 3 mm, no more than about 2 mm or even no more than about 1 mm.

A necking apparatus may have a necking die actuator to move a first die portion and/or second die portion to open the die for insertion of the preform tube or actuation of the tube through the necking die after an initial stretching of the first stretched portion. The necking die actuator may be controlled by a controller and may automatically open when required for insertion or advancement of the tube for processing. The necking die aperture may be slightly larger than the diameter of the stretched portions of the parison tube and may have a blunt orthogonal face to neck the tapered portion of the parison tube on the first and second end of the balloon portion.

An exemplary parison preform tube may be made out a polymeric material, such as a plastic and particularly a thermoplastic that can be melted or softened by heating and stretched including, but not limited to, polyethylene, polyester, polyamide, polyvinyl chloride, urethane and the like. A preform tube for the parison or the balloon diameter may be sized for entry into a conduit within the body, such as a vasculature conduit or digestive system conduit and may have a diameter of about 0.5 mm or more, 1 mm or more, 2 mm or more, 5 mm or more, 10 mm or more, 20 mm or more, 40 mm or more, 50 mm or more and any range between and including the diameters listed. The length of the balloon portion of the parison tube may be configured to expand a stent or stent graft and/or open a vessel within the body, such an artery or vein, or part of the digestive tract including intestine. The length of the balloon portion may be about 2 mm or more 5 mm or more, 10 mm or more, 20 mm or more, 40 mm or more, 50 mm, 75 mm or more, 100 mm or more and any range between and including the length values provided.

An exemplary parison former may incorporate a first and second tube retainer that are used to hold the ends of the preform tube. One or both of the tube retainers may move during the stretching operation to move the two tube retainers apart from each other. The tube retainers may be configured on a rail and may move along the rail by a tube retainer actuator. For example, a motor may move the tube retainer linearly along the rail. A rail may be any suitable guide for controlling the motion of the tube retainer along the length axis of the preform tube. An exemplary motor may be a stepper motor having very precise control of the amount of motion produced and the speed of motion, or speed of stretching produced. Furthermore, the preform may be stretched at a constant or variable speed and a stepper motor may enable a programmable rate of stretch to produce a uniform stretched portion with a desired tapered end on the balloon portion.

An exemplary radial compression heater may employ compression dies arranged around a central cavity as described in any one of U.S. Pat. No. 9,956,604, to Blockwise Engineering LLC, U.S. patent publication No. 2020/0384523, to Blockwise Engineering LLC; the entirety of each reference listed being incorporated by reference herein.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 3 shows the preform tube retained between a first tube retainer and a second tube retainer and a radial compression heater configured around the preform tube.

FIG. 4 shows the preform tube being stretched by the two retainers moving apart from each other, wherein the heated portion of the preform tube is stretched to form a first stretched portion.

FIG. 5 shows the preform tube being moved with respect to the radial compression heater to locate a new or second portion of the preform tube within the radial compression heater.

FIG. 6 shows this second portion of the preform tube being stretched by the two retainers moving apart from each other to form a parison tube having a balloon portion configured between the first stretched portion and the second stretched portion.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be an included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 1:
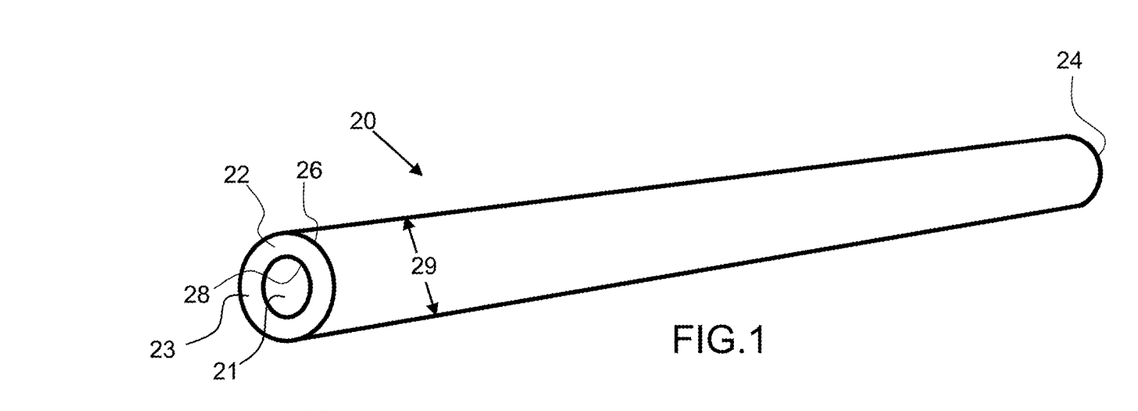
FIG. 1 shows a perspective view of an exemplary preform tube that is used to form a parison tube having a balloon portion.
Figure 2:
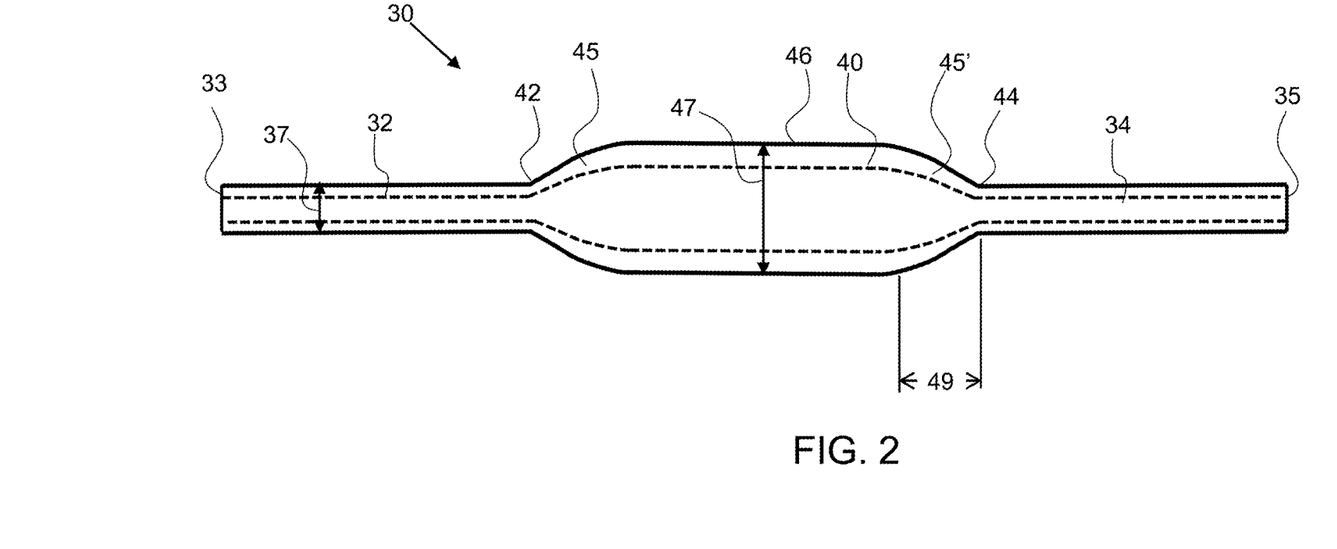
FIG. 2 shows a side view of an exemplary parison tube having a balloon portion configured between a first stretched portion and a second stretched portion.

Referring now to FIGS. 1 and 2, an exemplary parison tube 30, as shown in FIG. 2, is formed from a preform tube 20, shown in FIG. 1. The preform tube 20 is stretched to produce a reduced diameter tube or a first stretched portion 32 and a second stretched portion 34 with a balloon portion 40 configured therebetween. FIG. 1 shows a perspective view of an exemplary preform tube that is used to form a parison tube having a balloon portion. The preform tube has a wall 23 thickness from an outer surface 26 to an inner surface 28, a preform tube diameter 29 and a length from a first end 22 to a second end 24. The exemplary preform tube is cylindrical in shape, a cylinder that forms a conduit 21. The parison tube 30 has a balloon portion 40 that has a larger diameter 47 than the diameter 37 of the first and second stretched portions. The balloon portion 40 has tapered ends 45, 45' that taper down to the first stretched portion 32 and second stretched portion 34, respectively. The balloon portion 40 and has a length from first end 42 to the second end 44 of the balloon portion. The length 49 of the tapered ends may be minimized by uniform heating of the preform with the radial compression heater. The balloon portion has an outer surface 46. The parison tube may be cut to a desired length from a first stretched extended end 33 to a second stretched extended end 35.

Figure 3:
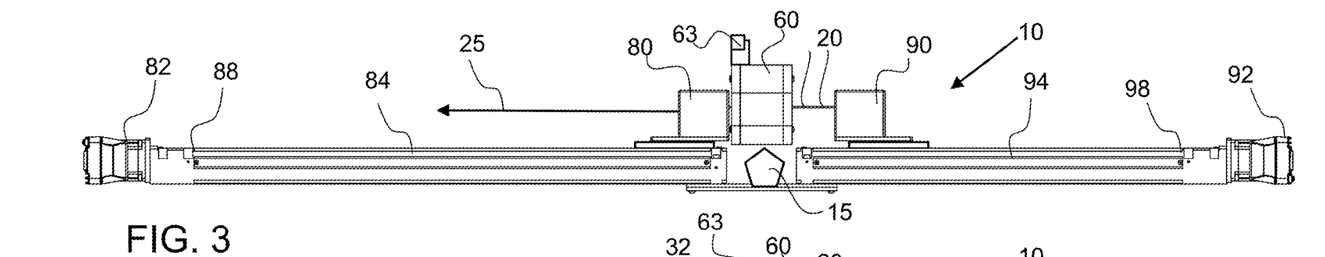
FIGS. 3 to 6 show an exemplary parison former forming a parison tube.
Figure 4:
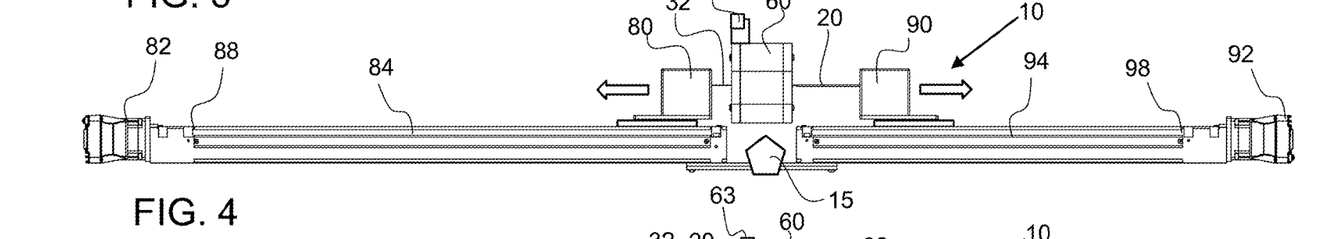

Referring now to FIGS. 3 to 6, an exemplary parison tube former 10 forms a parison tube 30 by selectively stretching the preform tube 20. As shown in FIG. 3, the preform tube 20 is retained between a first tube retainer 80 and a second tube retainer 90. The radial compression heater 60 is configured around the preform tube 20 to heat a first portion of the preform tube to enable stretching. The radial compression heater has an actuator 63 that closes the compression dies onto the outer surface of the preform tube to heat the preform tube through conduction, direct contact with the preform tube. After the tube is effectively heated, the preform tube is stretched, as shown in FIG. 4, to form a first stretched portion 32. The first tube retainer 80 and a second tube retainer 90 are moved apart from one another on a first rail 84 and a second rail 94, respectively. Note that moving apart may involve both tube retainers moving, or only one moving while the other remains stationary. A first tube retainer may be moved by a first tube retainer actuator 82, such as a servo motor that moves the first tube retainer along the first rail 84. Likewise, the second tube retainer 90 be moved by a second tube retainer actuator 92, such as a servo motor that moves the second tube retainer along the second rail 94. A servo motor may provide for very smooth motion and may enable the rate of stretching to be customized to produce uniform stretched portion of the preform tube.

Figure 5:
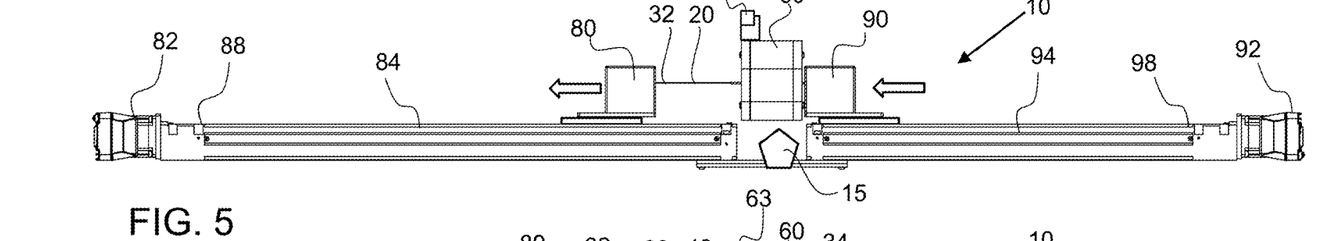
Figure 6:
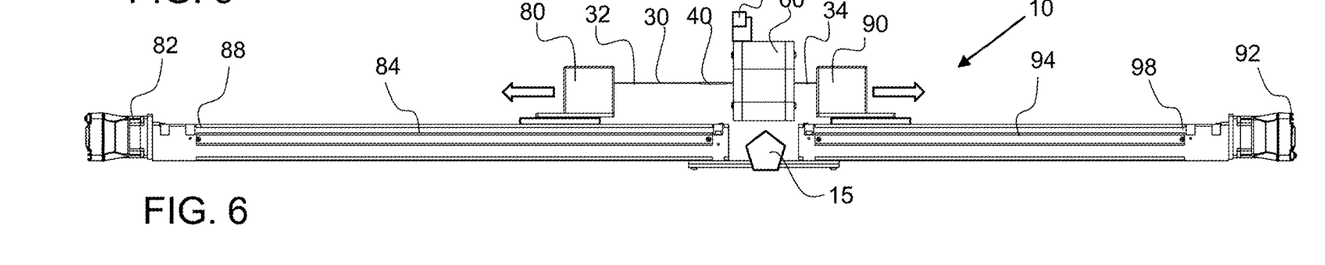

As shown in FIG. 5, the preform tube 20 is moved with respect to the radial compression heater to locate a new or second portion of the preform tube within the radial compression heater 60. A controller 15 may control the motion of the components to locate the second portion of the tube in the radial compression heater. The radial compression heater may be configured to move along the length axis 25, or length of the preform tube, or the first tube retainer and the second tube retainer may be configured to move the preform tube such that a second portion of the preform tube is configured within the radial compression heater. The radial compression heater may be on a rail, which may be the same rail as the first rail or second rail. A single rail may be used for example extending from a first rail end 88 to a second rail end 98. The die actuator will close down around this second portion of tube to apply heat again through conduction. The first tube retainer 80 and the second tube retainer 90 are moved apart from one another to produce a second stretched portion 34 and a balloon portion 40 between the first stretched portion 32 and said second stretched portion 34 of the parison tube 30, as shown in FIG. 6. Only one of the tube retainers, the second tube retainer 90 may be moved to move the first and second tube retainers apart from each other to form the second stretched portion 34.

Figure 7:
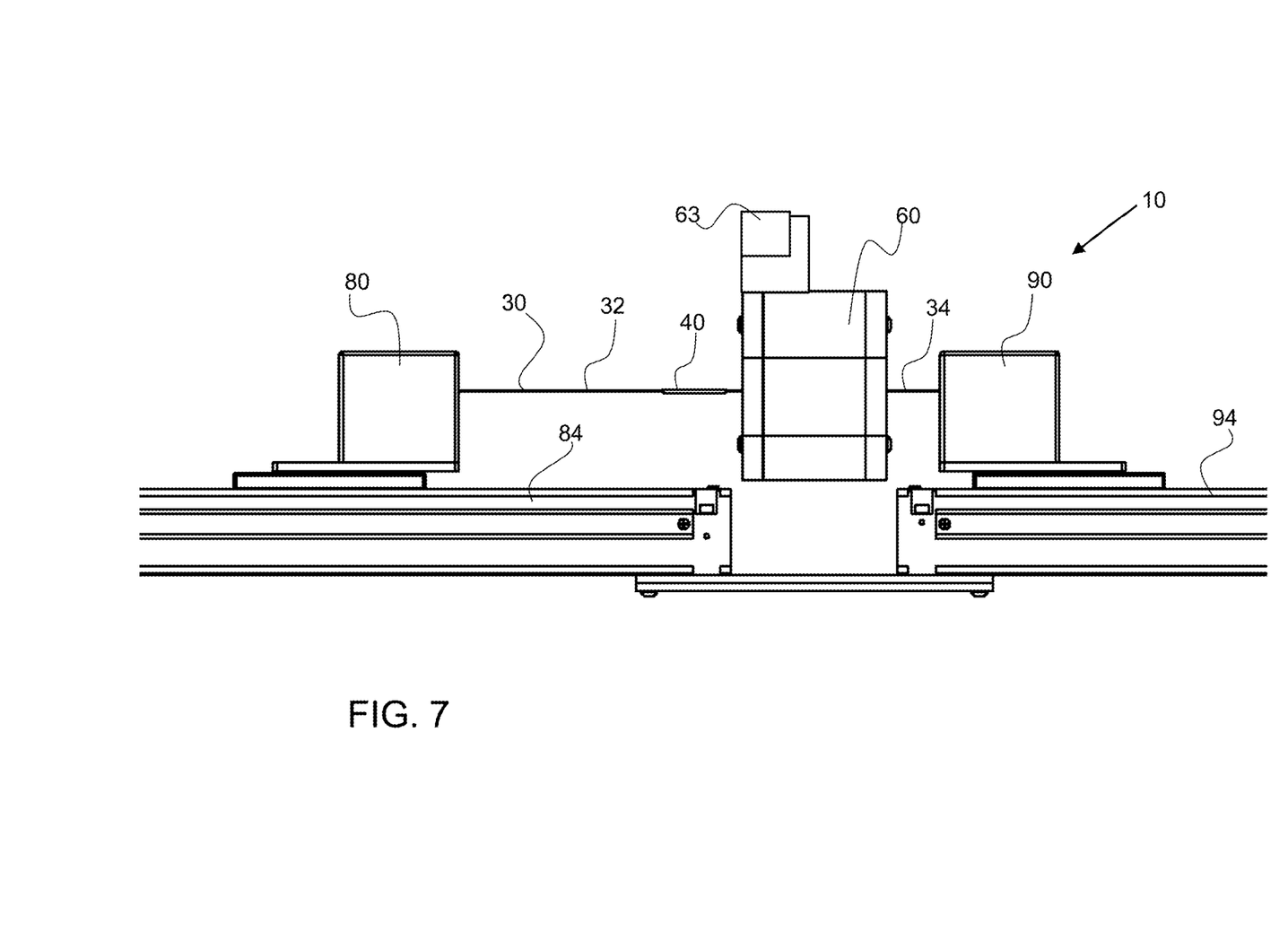
FIG. 7 shows an enlarged view of FIG. 6, wherein the balloon portion 40 is configured between the first stretched portion and the second stretched portion of the parison tube.

As shown in FIG. 7, the balloon portion 40 is configured between the first stretched portion 32 and the second stretched portion 34 of the parison tube 30. The parison tube is formed by iterative stretching and moving the perform tube by the first tube retainer 80 and the second tube retainer 90 to configured a second portion of the tube in the radial compression heater 60 after a first portion has been stretched to form the first stretched portion 32.

Figure 8:
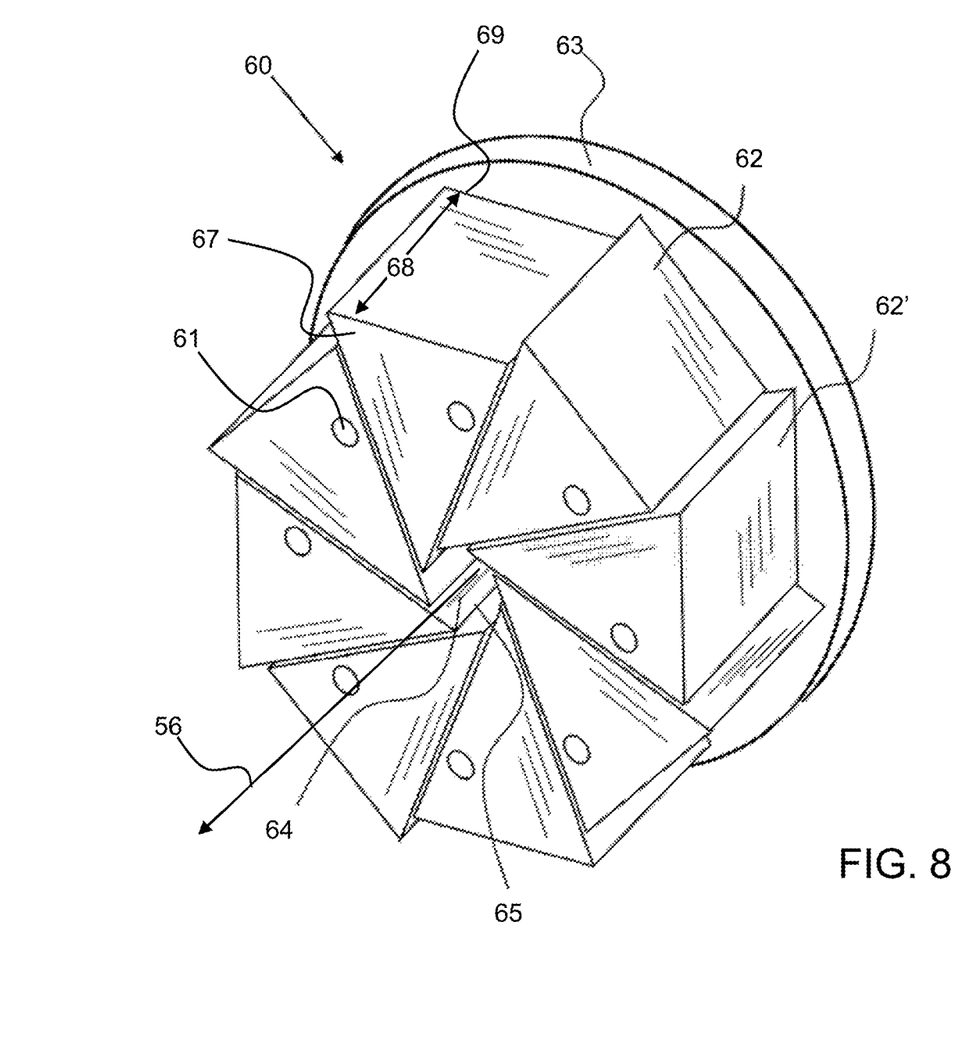
FIG. 8 shows an exemplary radial compression heater having a plurality of compression dies that move with respect to each other to form a central cavity that closes down onto a preform tube to heat said preform tube for stretching.

As shown in FIG. 8, an exemplary radial compression heater 60 has a plurality of compression dies 62, 62' arranged about a central axis 56, that move with respect to each other to form a central cavity 65, of the working surfaces 64, that close down onto a preform tube to heat said preform tube for stretching. The compression dies, or central cavity 65 formed therefrom, produce a first end 67 and a second end 69 of the radial compression heater 60, and have a length 68 to receive a preform tube. One or more heaters 61 may be configured to heat the compression dies.

Figure 9:
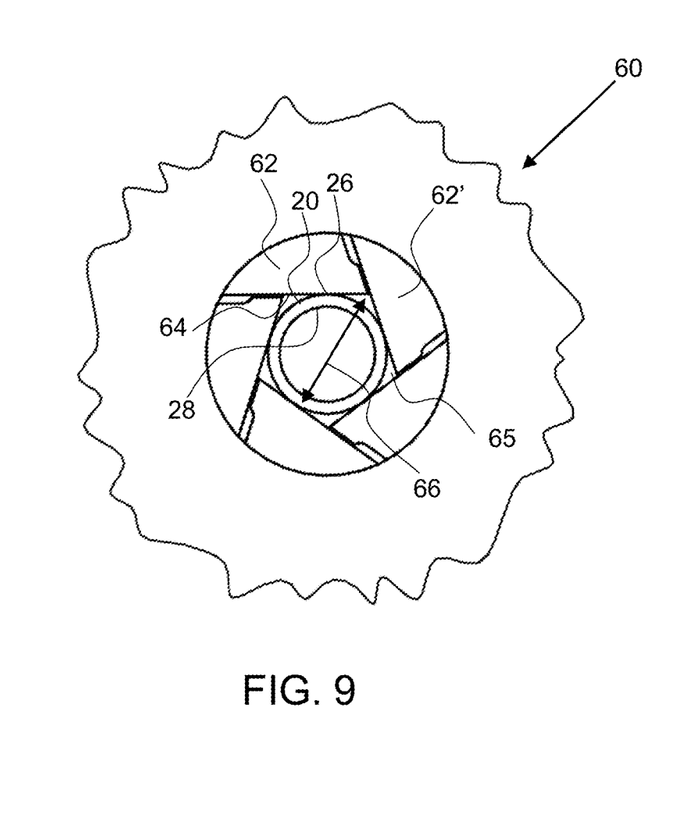
FIG. 9 shows a first end view of a radial compression heater configured around a preform tube to heat said preform tube.

As shown in FIG. 9, an exemplary radial compression heater 60 is configured around a preform tube 20 to heat said preform tube. The working surfaces 64 of the compression dies 62 form a central cavity 65, having a central cavity diameter 66, that is in contact with the outer surface 26 of the preform tube. The preform tube is heated by conduction and direct contact with the working surfaces 64.

Figure 10:
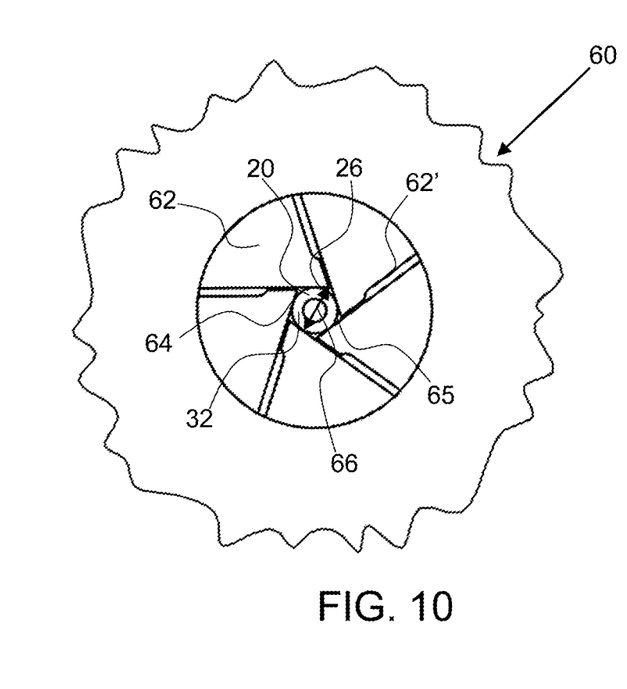
FIG. 10 shows a first end view of the radial compression heater shown in FIG. 9 after the preform tube has been stretched, wherein the compression dies move radially inward with the stretching tube to continue to heat the tube by conduction during the stretching process.

As shown in FIG. 10, the exemplary radial compression heater 60 is configured around a first stretched portion 32 of a preform tube 20 to continue to heat said preform tube as it is being stretched. The working surfaces 64 of the compression dies 62 form a central cavity 65, having a central cavity diameter 66, that is in contact with the outer surface 26 of the preform tube. The compression dies may be forced inward by a die actuator to reduce the central cavity diameter and press the working surfaces into contact with the outer surface of the preform tube as it is stretched and reduced in diameter, as shown.

Figure 16:
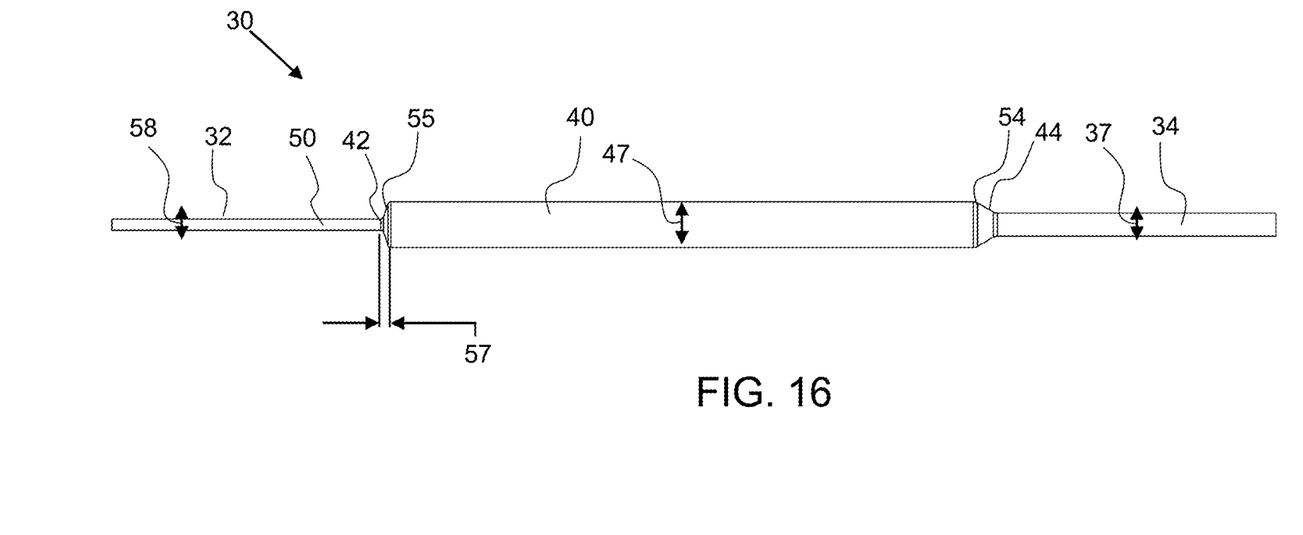
FIG. 16 shows a side view of a parison tube having a balloon portion between a first stretched portion and a second stretched portion and having one necked balloon end and one other end that has not been necked.

Referring now to FIGS. 11 to 14, a radial compression heater 60 may be configured with a necking apparatus 70 configured on the opening into the radial compression heater and comprising a necking die 72 that is configured to open for insertion of the preform tube 20 into the necking die aperture 76 and configured to close to enable necking the diameter and tapered end of the balloon portion to produce a necked balloon end 55, shown in FIG. 16. The necking apparatus 70 may be configured on a first end 67 and/or second end 69 of the radial compression heater 60. The necking die 72 has a first die portion 73 and a second die portion 74.

Figure 11:
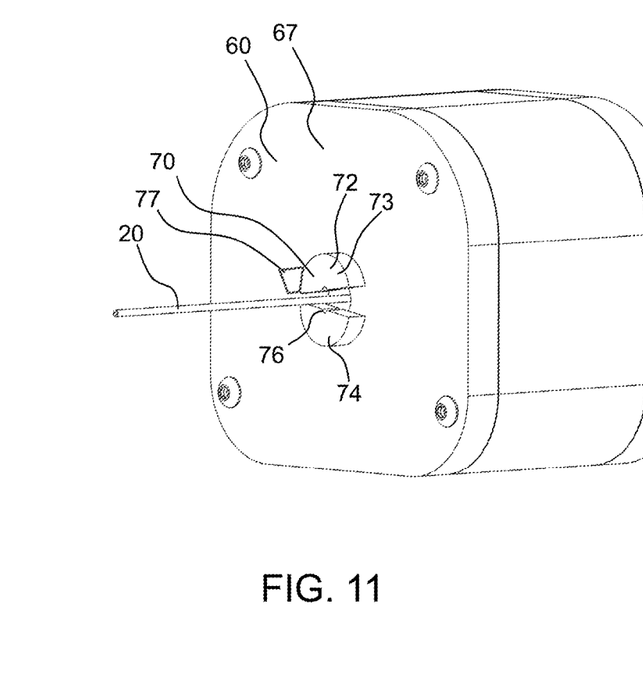
FIG. 11 shows a first end of a radial compression heater with a necking apparatus configured on the opening into the radial compression heater and comprising a necking die in an open configuration to enable insertion of the parison tube therein and subsequent necking the tapered end of the balloon portion.

As shown in FIG. 11, the first die portion 73 and second die portion 74 of the necking die 72 are in an open configuration to enable insertion of the preform tube. The necking die has a necking die actuator 77 configured to open the necking die 72 for insertion of the perform tube 20, or movement of the partially processed parison tube through the necking die, such as after the first stretch to advance the tube to locate a second portion for heating and stretching.

Figure 12:
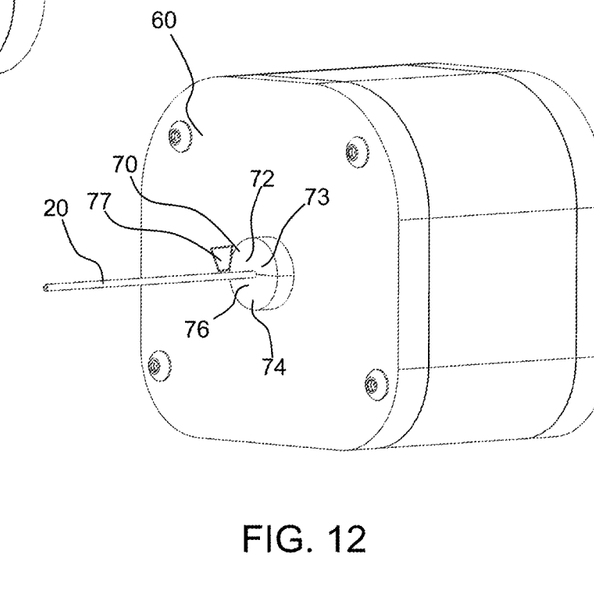
FIG. 12 shows the first end of a radial compression heater shown in FIG. 11 with the necking die now in a closed configuration to enable necking the tapered end of the balloon portion to produce a necked balloon end.
Figure 13:
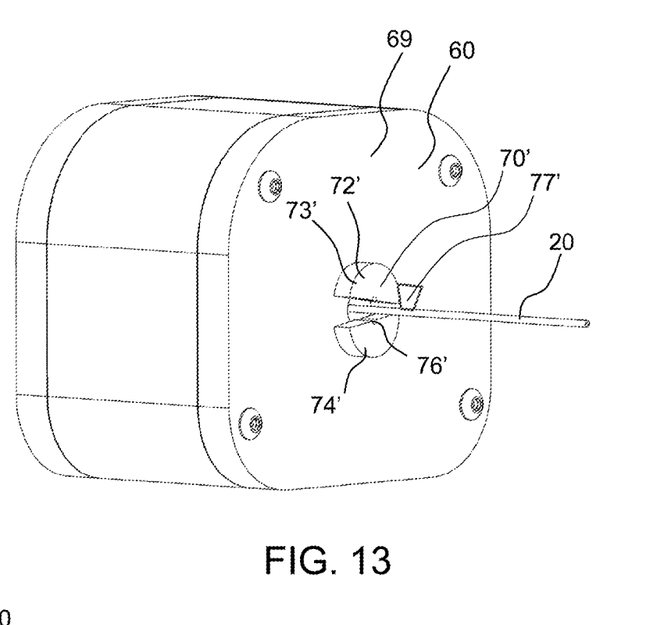
FIG. 13 shows a second end of a radial compression heater with a necking apparatus configured on the opening into the radial compression heater and comprising a necking die in an open configuration to enable insertion of the parison tube therein and subsequent necking the tapered end of the balloon portion.
Figure 14:
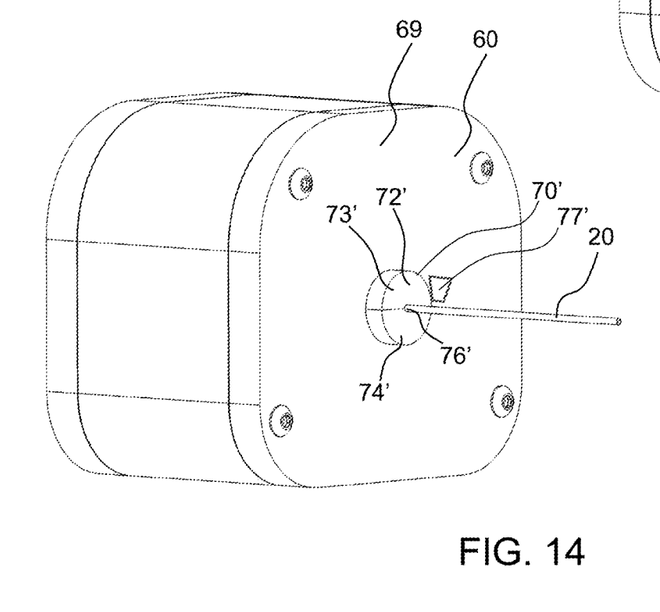
FIG. 14 shows the first end of a radial compression heater shown in FIG. 13 with the necking die now in a closed configuration to enable necking the tapered end of the balloon portion to produce a necked balloon end.

As shown in FIG. 12 the first die portion 73 and second die portion of the necking die 72 are in a closed configuration to produce a necked balloon end by pulling the stretched portion through the necking die aperture 76 and the balloon portion against the closed necking die 72. FIGS. 11 and 12 show the first end 67 of the radial compression heater 60 and FIGS. 13 and 14 show the second end 69 of the radial compression heater 60, also having a necking apparatus 70' with a necking die 72' with a first die portion 73' and second die portion 74' forming a second die aperture 76' and a necking die actuator 77'.

Figure 15:
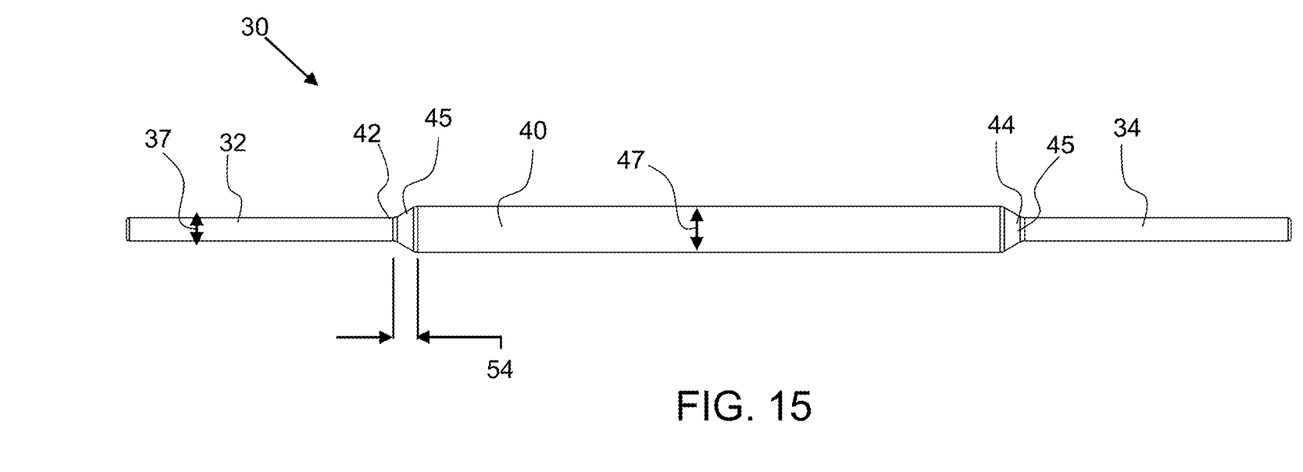
FIG. 15 shows a side view of a parison tube having a balloon portion between a first stretched portion and a second stretched portion and having tapered ends on either end of the balloon portion between the balloon portion and the first stretched portion and a second stretched portion.

As shown in FIG. 15, a parison tube 30 has a balloon portion 40 between a first stretched portion 32 and a second stretched portion 34 and has tapered ends 45, 45' on the first end 42 and second end 44 of the balloon portion between the balloon portion and the respective first stretched portion and a second stretched portion. The tapered ends have a tapered end length 54 wherein the parison tapers from the balloon portion to the first stretched portion 32 and the respective second stretched portion 34. The tapered ends taper from the balloon portion diameter 47 to the stretched portion diameter 37.

As shown in FIG. 16, a parison has a balloon portion 40 between a first stretched portion 32 that has been necked by the necking apparatus to produce a necked tube portion 50, and the parison tube has a second stretched portion 34 that has not been necked. The tapered end length 54 on the second end 44 of the balloon portion 40 is longer than the necked end length 57 on the first end 42 of the balloon portion. Also, the necked tube diameter 58 is less than the stretched portion diameter 37 of the second stretched portion 34, which has not been necked. The necked balloon end length 57 is a fraction of the tapered end length 54.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A parison tube former comprising:
a) a first tube retainer;
b) a second tube retainer;
c) a radial compression heater comprising:
  i) a plurality of compression dies each having a working surface,
  wherein the plurality of compression dies are arranged radially with respect to each other to form a central cavity defined by said working surfaces, wherein the central cavity has a central cavity diameter;
  ii) a heater configured to heat the compression dies;
  iii) a die actuator configured to move the plurality of compression inward to reduce the central cavity diameter;
d) a preform tube extending through the central cavity of the radial compression heater and having a length between the first tube retainer and the second tube retainer;
wherein the radial compression heater is configured to heat a portion of the length the preform tube between the first tube retainer and the second tube retainer,
wherein the plurality of compression dies are configured to close down onto the outer surface of the preform tube, wherein the working surface of said plurality of compression dies contact the preform tube to heat a portion of said length of the preform tube; and
wherein the first tube retainer and second tube retainer are configured to move apart from each other to stretch the preform tube and from said parison tube having a balloon portion configured between a first stretched portion and a second stretched portion.

2. The parison tube former of claim 1, further comprising:
a rail and wherein the first tube retainer is configured on said rail; and
a first tube retainer actuator wherein said first tube retainer is actuated along said rail by said first tube retainer actuator.

3. The parison tube former of claim 1, further comprising:
a rail and wherein the second tube retainer is configured on said rail; and
a second tube retainer actuator wherein said second tube retainer is actuated along said rail by said second tube retainer actuator.

4. The parison tube former of claim 1, wherein the preform tube comprises a thermoplastic polymer.

5. The parison tube former of claim 1, further comprising:
e) a first necking apparatus configured on an end of the radial compression heater comprising:
  i) a necking die configured to move from an open configuration to a closed configuration;
    wherein the necking die is configured in an open configuration to receive said preform tube into the heater;
    wherein the necking die is configured to close after stretching the preform tube; and
    wherein said first stretched portion is configured for actuation through the necking die to reduce a diameter of the first stretched portion by at least 5% and then press a first end of said balloon portion against the necking die to neck the first end of the balloon portion to produce a first necked end of the balloon portion.

6. The parison tube former of claim 1, wherein the first tube retainer and the second tube retainer move in opposing directions to stretch the preform tube to form the first stretched portion.

7. The parison tube former of claim 1, wherein only one of the first tube retainer and the second tube retainer moves to stretch the preform tube to form the second stretched portion.

8. The parison tube former of claim 1, wherein the working surfaces of the plurality of dies are forced by the die actuator radially inward to reduce the central cavity diameter while the preform tube is stretched.

9. The parison tube former of claim 1, wherein a second portion of the preform tube is configured to be located within the radial compression heater after the first stretched portion is produced and wherein the radial compression heater is configured to heat said second portion before the first tube retainer and second tube retainer are configured to move apart from each other to stretch the preform tube and produce said second stretched portion and said balloon portion of said parison tube.

10. The parison tube former of claim 9, wherein the first tube retainer and second tube retainer are configured to move the preform tube to locate said second portion of the preform tube within the radial compression heater.

11. The parison tube former of claim 5, wherein said second stretched portion is configured for actuation through the necking die to reduce a diameter of the second stretched portion and press a second end of a balloon portion against the necking die to neck the second end of the balloon portion to produce a second necked end of the balloon portion.

12. The parison tube former of claim 5, wherein the first necking apparatus comprises a necking die actuator configured to move the necking die from said closed configuration to said open configuration.

13. The parison tube former of claim 12, wherein the necking die of the first necking apparatus comprises a first die portion and a second die portion forming a die aperture therebetween when in said closed configuration.

14. The parison tube former of claim 5 wherein said first necking apparatus is configured on a first end of the radial compression heater and wherein a second necking apparatus is configured on a second end of the radial compression heater, said second necking apparatus comprising:
   i) a necking die configured to move from an open configuration to a closed configuration;
      wherein said necking die of the second necking apparatus is configured in an open configuration to receive said preform tube into the heater;
      wherein the necking die of the second necking apparatus is configured to close after stretching the preform tube to produce said second stretched portion; and
   wherein said second stretched portion is configured for actuation through the necking die to reduce to diameter of the second stretched portion and press a second end of said balloon portion against the necking die of the second necking apparatus to neck the second end of the balloon portion to produce a second necked end of the balloon portion.

15. The parison tube former of claim 14, wherein the first necking apparatus and the second necking apparatus each comprises a necking die actuator configured to move the respective necking die from said closed configuration to said open configuration.

16. The parison tube former of claim 14, wherein the necking die of the first necking apparatus and the second necking apparatus each comprise a first die portion and a second die portion forming a die aperture therebetween when in said closed configuration.

17. The parison tube former of claim 5, wherein the necking die reduces the diameter of the first stretched portion by at least 20% to produce said necked tube diameter.

18. The parison tube former of claim 17, wherein a first tapered end, having a first tapered end length, is configured between a first balloon end and the first stretched portion and wherein the first necking apparatus is configured to produce a first necked end length that is half or less said first tapered end length.

19. The parison tube former of claim 5, wherein a first tapered end, having a first tapered end length, is configured between the first balloon end and the first stretched portion and wherein the first necking apparatus is configured to produce a first necked end length that is half or less said first tapered end length.

* * * * *